(12) United States Patent  (10) Patent No.: US 9,414,886 B2
Varney  (45) Date of Patent: Aug. 16, 2016

(54) ELECTROSURGICAL ELECTRODE

(75) Inventor: Kelvin John Varney, Abergavenny (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 259 days.

(21) Appl. No.: 14/128,893

(22) PCT Filed: Jun. 18, 2012

(86) PCT No.: PCT/GB2012/000527
§ 371 (c)(1),
(2), (4) Date: Feb. 26, 2014

(87) PCT Pub. No.: WO2012/175912
PCT Pub. Date: Dec. 27, 2012

(65) Prior Publication Data
US 2014/0214021 A1 Jul. 31, 2014

(30) Foreign Application Priority Data
Jun. 23, 2011 (GB) .................................. 1110646.5

(51) Int. Cl.
A61B 18/14 (2006.01)
A61B 18/18 (2006.01)
A61B 18/00 (2006.01)

(52) U.S. Cl.
CPC ............... *A61B 18/18* (2013.01); *A61B 18/149* (2013.01); *A61B 18/1445* (2013.01); *A61B 2018/00601* (2013.01); *A61B 2018/00625* (2013.01);
(Continued)

(58) Field of Classification Search
CPC .. A61B 18/1445; A61B 18/149; A61B 18/18; A61B 2018/00601; A61B 2018/00625; A61B 2018/1407; A61B 2018/1417
See application file for complete search history.

(56) References Cited

U.S. PATENT DOCUMENTS 3,901,242 A * 8/1975 Storz ........................ A61B 1/12
606/46
4,917,082 A 4/1990 Grossi et al.
(Continued)

FOREIGN PATENT DOCUMENTS

CN 2617327 Y 5/2004
CN 101035478 A 9/2007
(Continued)

OTHER PUBLICATIONS

International Search Report issued in International Patent Application No. PCT/GB2012/000527 dated Sep. 10, 2012.
(Continued)

*Primary Examiner* — Daniel Fowler
(74) *Attorney, Agent, or Firm* — Oliff PLC

(57) ABSTRACT

An electrode is for use in an electrosurgical probe, the electrode having two arms defining a longitudinal direction. The electrode also includes a loop depending from the two arms and defining a cutting area within the loop, and a vaporization member attached to one side of the loop. The vaporization member is such that it does not occlude the cutting area and yet presents a substantial profile when the electrode is moved in the longitudinal direction. The arrangement is such that when the electrode is moved in a first longitudinal direction, the loop is capable of resecting a sample of tissue. When the electrode is moved in the opposite longitudinal direction, the vaporization member is capable of vaporizing tissue adjacent thereto to form a groove therein.

17 Claims, 15 Drawing Sheets

Figure 1:
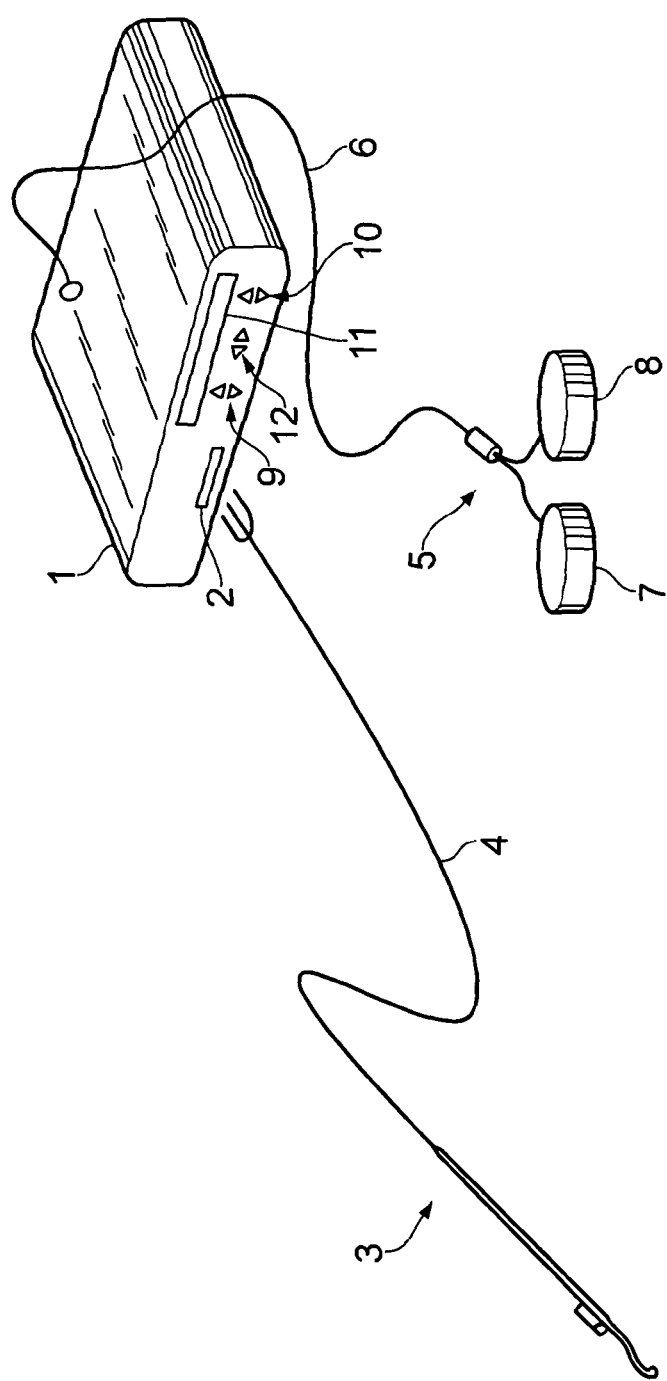

(52) U.S. Cl.
CPC . *A61B2018/1407* (2013.01); *A61B 2018/1417* (2013.01)

(56) References Cited

U.S. PATENT DOCUMENTS

| | | | |
|---|---|---|---|
| 5,007,907 A | | 4/1991 | Nishigaki et al. |
| 5,064,424 A | | 11/1991 | Bitrolf |
| 5,549,605 A | | 8/1996 | Hahnen |
| 5,766,168 A | | 6/1998 | Mantell |
| 5,843,019 A | * | 12/1998 | Eggers .................. A61B 18/12 604/114 |
| 5,919,189 A | | 7/1999 | Benderev |
| 5,919,191 A | * | 7/1999 | Lennox .................. A61B 18/14 606/46 |
| 5,935,125 A | | 8/1999 | Zupkas |
| 6,033,400 A | | 3/2000 | Grossi et al. |
| 6,322,494 B1 | | 11/2001 | Bullivant et al. |
| 6,730,081 B1 | | 5/2004 | Desai |
| 7,211,081 B2 | | 5/2007 | Goble |

FOREIGN PATENT DOCUMENTS

| | | |
|---|---|---|
| EP | 1656900 A2 | 5/2006 |
| EP | 1 974 683 A1 | 10/2008 |
| WO | WO 96/32898 A1 | 10/1996 |
| WO | WO 97/23169 A1 | 7/1997 |

OTHER PUBLICATIONS

Written Opinion of the International Searching Authority issued in International Patent Application No. PCT/GB2012/000527 dated Sep. 10, 2012.

Oct. 20, 2011 British Search Report issued in British Application No. 1110646.5.

Jul. 21, 2015 Office Action issued in Chinese Patent Application No. 201280031105.2.

\* cited by examiner

ELECTROSURGICAL ELECTRODE

This invention relates to an electrosurgical electrode and in particular to an electrode for use in a system for endoscopic urological surgery using a resectoscope. Such systems are well known in the art, examples being given in U.S. Pat. Nos. 5,007,907 and 6,322,494. Such systems include an electrosurgical instrument deployable by means of a resectoscope, and an electrosurgical generator powering the instrument. A generator suitable for powering a urological instrument is described in U.S. Pat. No. 7,211,081. Instruments used in electrosurgical urology surgery are either bipolar, in which case two electrodes are present at the distal end of the instrument, or monopolar, in which case one electrode is present on the instrument and a second electrode is provided in the form of a patient return plate.

Different types of electrodes have been used previously depending on their intended function. Loop electrodes (see U.S. Pat. No. 4,917,082 as an example) are generally good for tissue resection, while roller electrodes (see U.S. Pat. No. 5,549,605 as an example) or slider electrodes (see U.S. Pat. No. 5,766,168 as an example) are used for vaporisation and/or coagulation of tissue. The present invention attempts to provide a different electrode capable of efficient tissue resection and vaporisation/coagulation.

According to a first aspect of the invention, there is provided an electrode for use in an electrosurgical probe, the electrode comprising two arms defining a longitudinal direction, a loop extending laterally from the two arms and defining a cutting area within the loop, and an electrically conductive vaporisation member attached to and electrically connected to one side of the loop such that when the loop is supplied with RF energy the vaporisation member is also energised, the vaporisation member being such that it does not occlude the cutting area and yet presents a substantial profile when the electrode is moved axially in the longitudinal direction, the arrangement being such that when the electrode is energised and moved in a first longitudinal direction, the loop is capable of resecting a sample of tissue, the resected tissue being received within the cutting area, and when the electrode is energised and moved in the opposite longitudinal direction, the vaporisation member is capable of vaporising tissue adjacent thereto to form a groove therein.

The disclosed electrode is optimised for both tissue resection and vaporisation. The loop provides effective tissue resection, while the vaporisation member provides effective tissue vaporisation, or alternatively tissue coagulation if a coagulating signal is supplied to the electrode. Previous attempts to combine tissue resection and vaporisation include U.S. Pat. No. 5,064,424. This patent provides a partly spherical electrode, with a cutting loop upstanding from a central flat face of the electrode. The electrode disclosed hereinafter differs from this arrangement in that the vaporisation member is attached to a side face of the loop, such that the loop is provided at the front or rear face of the electrode. This allows for effective tissue resection when the electrode is moved in a first longitudinal direction, and for effective tissue vaporisation when the electrode is moved in an opposite longitudinal direction. Unlike U.S. Pat. No. 5,064,424, in which the instrument would need to be rotated 180 degrees in order to change the action of the instrument, the present electrode merely needs a change of longitudinal direction in order to completely change the tissue effect.

The vaporisation member is conveniently in the form of a leaf member having an upper surface and a lower surface, and the upper surface of the vaporisation member terminates adjacent the loop. This ensures that the vaporisation member does not interfere with the cutting action of the loop. The term "loop" is meant to include any shape starting and finishing at the two arms, and extending below the arms. The loop does not need to be U-shaped, but can be a parabola, V-shaped, or any other convenient shape, including three sides of a square or rectangle. Preferably, the loop includes a lowest point which is furthest from the two arms, and the lower surface of the vaporisation member extends upwardly from the lowest point of the loop so as to terminate at a height between the arms and the lowest point of the loop. This upwardly extending structure serves two purposes, the first being to increase the profile of the vaporisation member presented to the tissue, so as to make possible the removal of a groove of tissue when the electrode is moved longitudinally with respect thereto. The second purpose of the upward profile is to guide upwardly "chips" of tissue being cut with the loop, when the electrode is moved in the opposite longitudinal direction. The upward profile urges the tissue up and away from the loop, providing the user with good visibility and preventing removed tissue from becoming tangled with the remainder of the electrosurgical instrument.

According to a preferred embodiment, the vaporisation member includes a curved portion of a shape formed by sweeping an arc with a curve equivalent to at least a section of the loop member. This provides a smooth transition from the loop to the vaporisation member, allowing tissue to pass either side of the loop when it is cutting through tissue. Preferably, the curved portion of the vaporisation member is of a shape formed by sweeping an arc of at least 45 degrees, conveniently at least 90 degrees, and conceivably at least 120 degrees. Conveniently (but not necessarily), the curved portion of the vaporisation member forms part of the surface of a sphere.

The curved portion conceivably constitutes the entirety of the vaporisation member, or it may alternatively constitute only a portion of the vaporisation member. Where the curved portion constitutes only a portion of the vaporisation member, the vaporisation member also conveniently includes a linear, upwardly sloping section. The curved portion is conveniently located between the loop and the upwardly sloping section, such that the linear section provides both the "depth" for the electrode to vaporise a groove of tissue, and also the "run-off" for chips of tissue cut by the loop. Preferably, the cross-sectional thickness of the vaporisation member is substantially constant.

The loop extends laterally from the two arms, but not necessarily at an angle of 90 degrees. According to a convenient embodiment, the loop extends laterally at an angle of between 60 and 120 degrees with respect to the two arms. In one arrangement, the loop extends laterally at an angle of less than 90 degrees from the two arms, such that it has an acute angle with respect to the arms. Alternatively, the loop extends laterally at an angle of greater than 90 degrees from the two arms, such that it creates an obtuse angle with the arms. However, the loop may conceivably extend laterally at an angle of substantially 90 degrees from the two arms.

In one arrangement, the vaporisation member is attached to the loop on the same side as the two arms. This is to say, with the arms extending longitudinally from a proximal end to a distal end, and with the electrode attached at the distal end of the arms, the vaporisation member lies on the proximal side of the loop. This means that the loop will cut tissue when the electrode is moved in a distal direction, and the vaporisation member will form a groove in the tissue when the electrode is moved in a proximal (or retrograde) direction.

Alternatively, the vaporisation member is attached to the loop portion on the opposite side from the two arms. This is to say that the vaporisation member lies on the distal side of the loop, such that the loop will cut tissue when the electrode is moved in a proximal direction, and the vaporisation member will form a groove in the tissue when the electrode is moved in a distal direction. These two alternatives are provided to take into account the preferences of individual surgeons, some of whom prefer to vaporise and some who prefer to cut tissue in a proximal direction.

The electrode preferably forms part of a bipolar electrode assembly in which the electrosurgical probe is provided with a return electrode insulated from the arms and the loop. Bipolar electrosurgical instruments have the advantage that electric current flows directly between the two electrodes, which are both located on the instrument shaft. Alternatively, the electrode forms part of a monopolar electrosurgery system in which the system is provided with a return patient plate electrode separate from the arms and the loop.

According to a second aspect of the invention, a hybrid electrode for an electrosurgical probe comprises two support arms defining a longitudinal direction, an electrically conductive cutting loop extending laterally from the arms to define a resection area within the loop, and, integral with the loop, an electrically conductive leaf member having one edge forming at least a section of the loop which is spaced from the arms, the leaf member extending from the said edge both longitudinally on one side of the loop and in a direction towards the arms so as to provide a conductive vaporisation surface. Typically, in a plane perpendicular to the arms the projected area of the leaf member is of a width substantially equal to the width of the loop.

The invention further resides in a method of treating tissue comprising the steps of i) presenting an electrode to the tissue to the treated, the electrode comprising two arms defining a longitudinal direction, a loop extending laterally from the two arms and defining a cutting area within the loop, and an electrically conductive vaporisation member attached to and electrically connected to one side of the loop such that when the loop is supplied with RF energy the vaporisation member is also energised, the vaporisation member being such that it does not occlude the cutting area and yet presents a substantial profile when the electrode is moved axially in the longitudinal direction, ii) energising the electrode with RF energy, iii) moving the electrode in a first longitudinal direction such that the loop resects a sample of tissue, the resected tissue being received within the cutting area, and iv) moving the electrode in the opposite longitudinal direction, such that the vaporisation member vaporises tissue adjacent thereto to form a groove therein.

Figure 2:
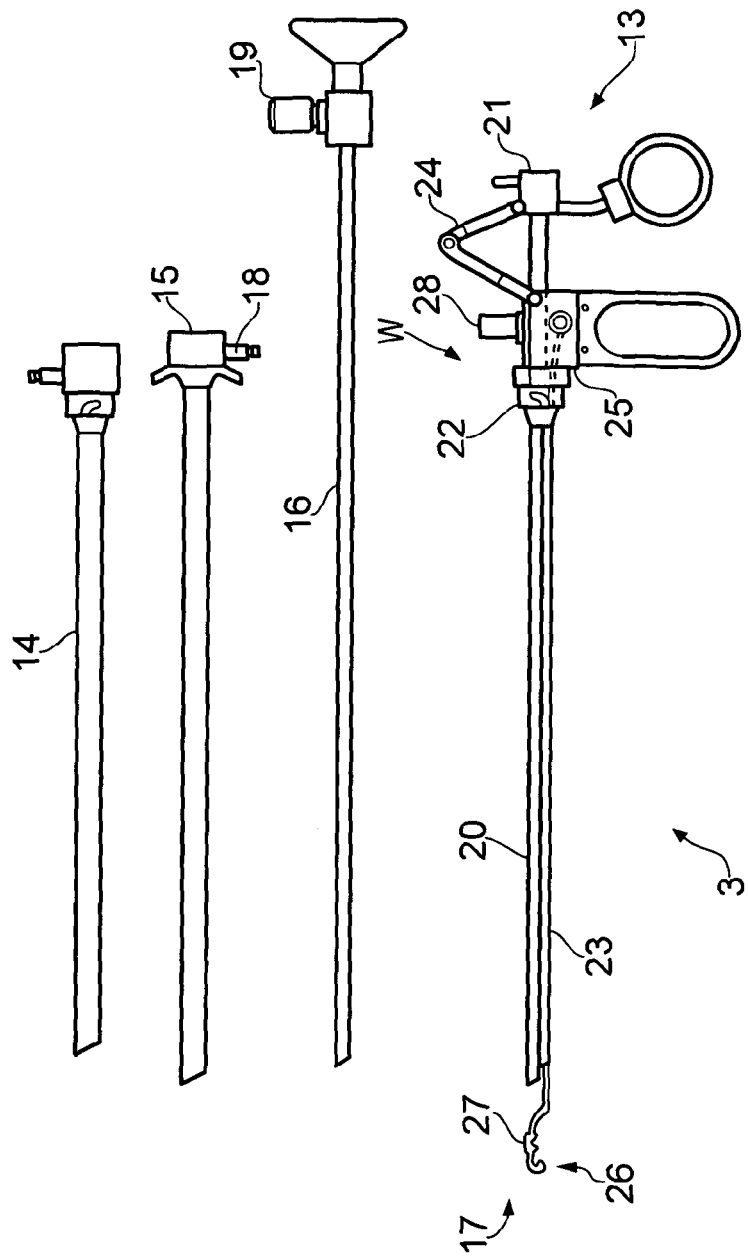
Figure 3:
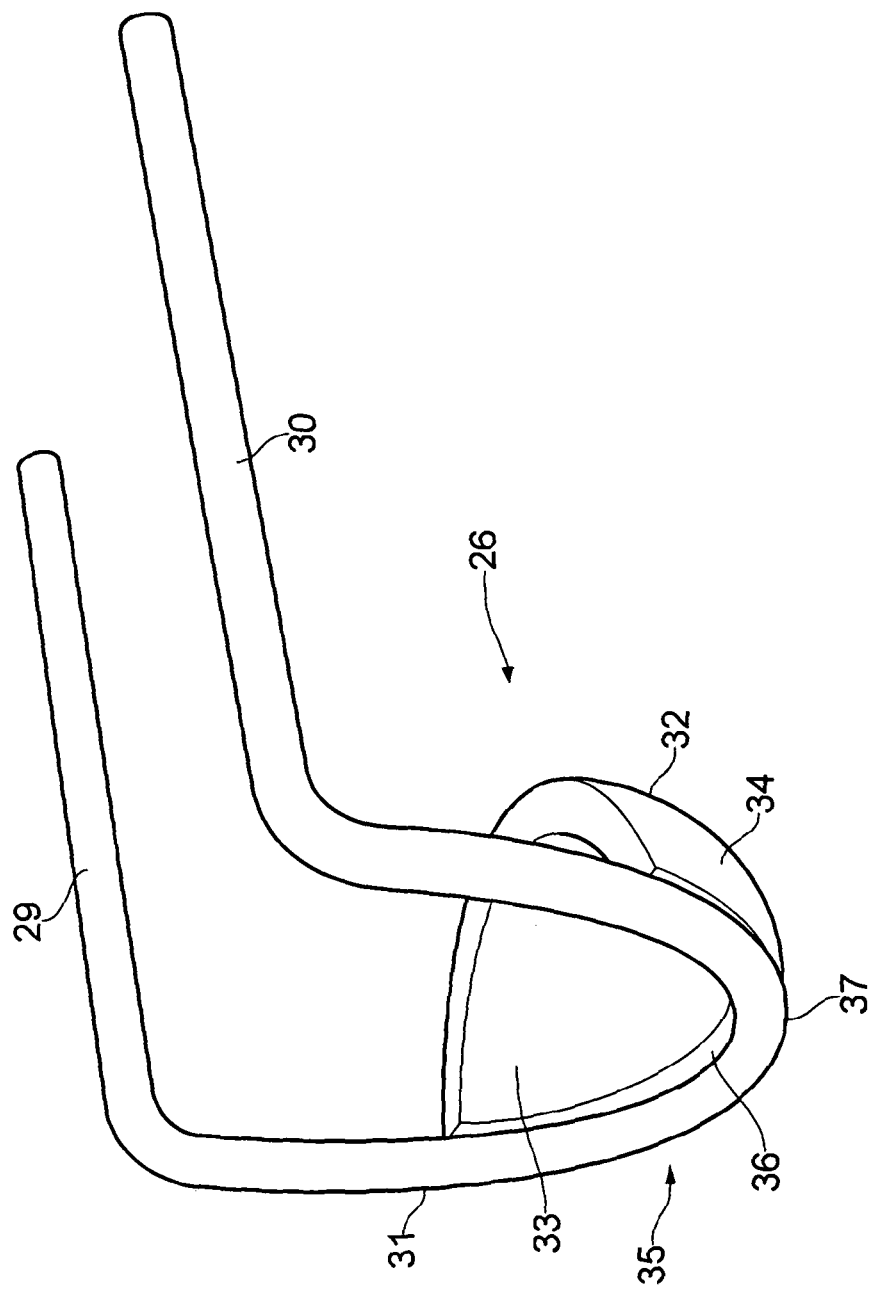
Figure 4:
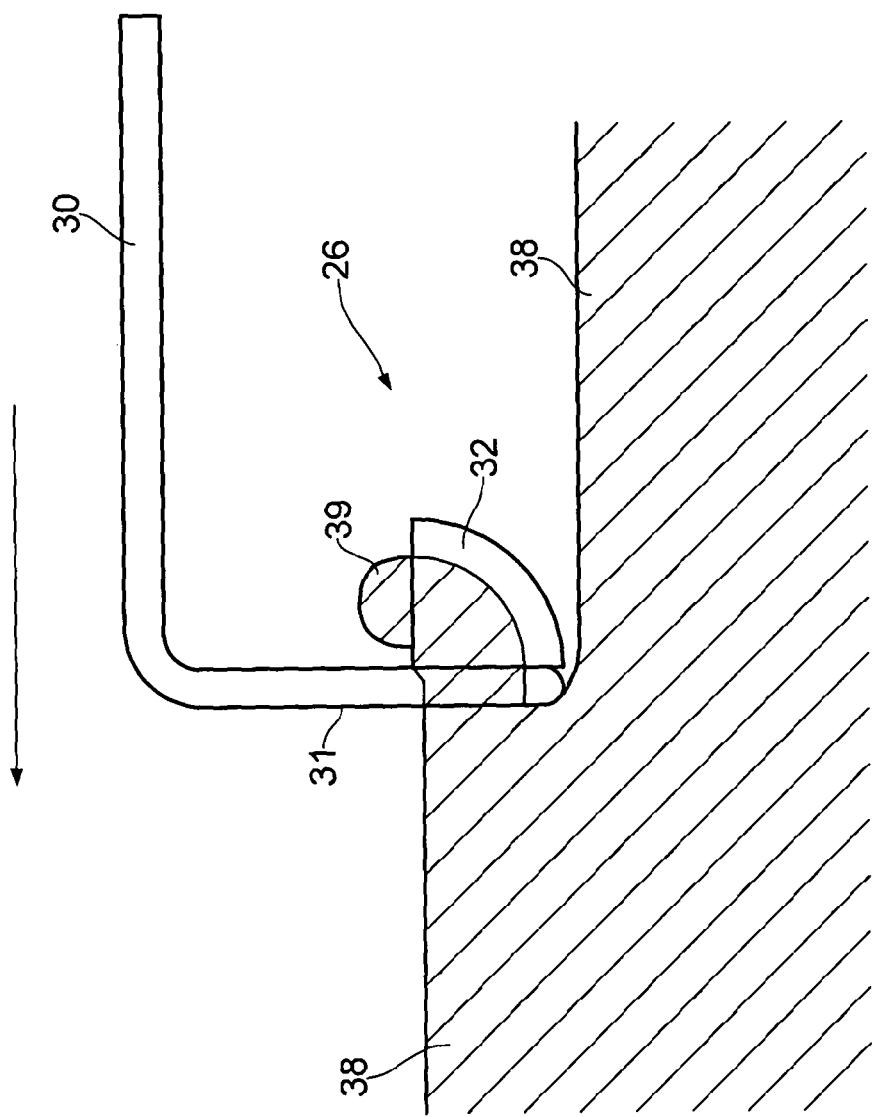
Figure 5:
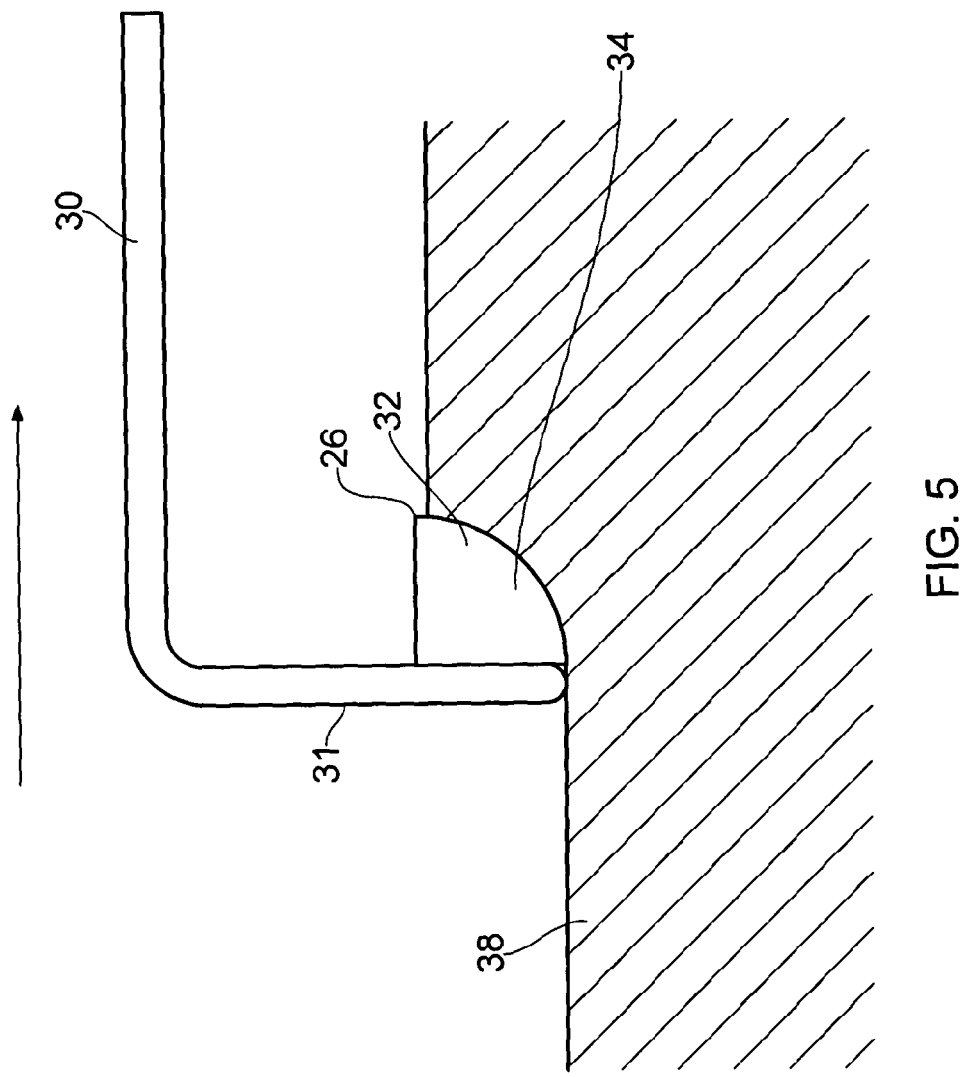
Figure 6:
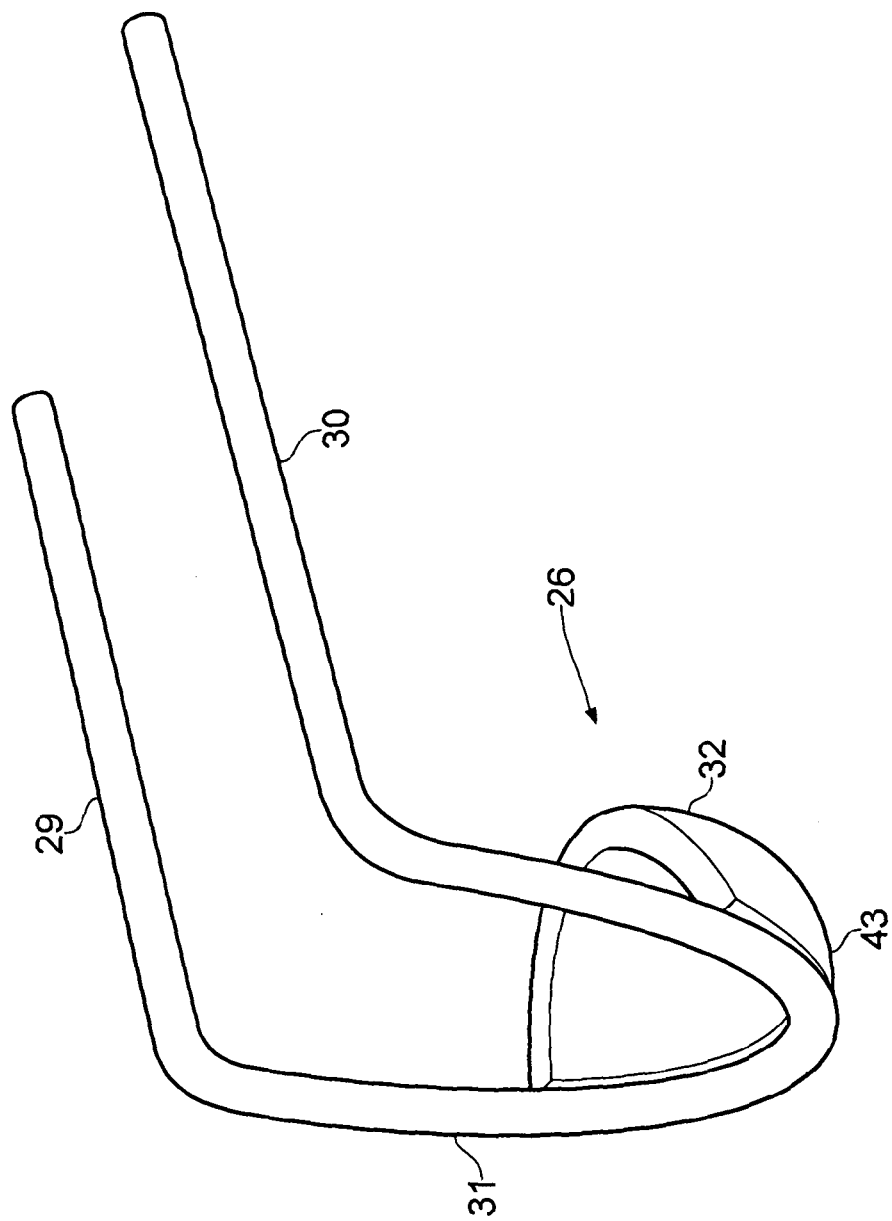
Figure 7:
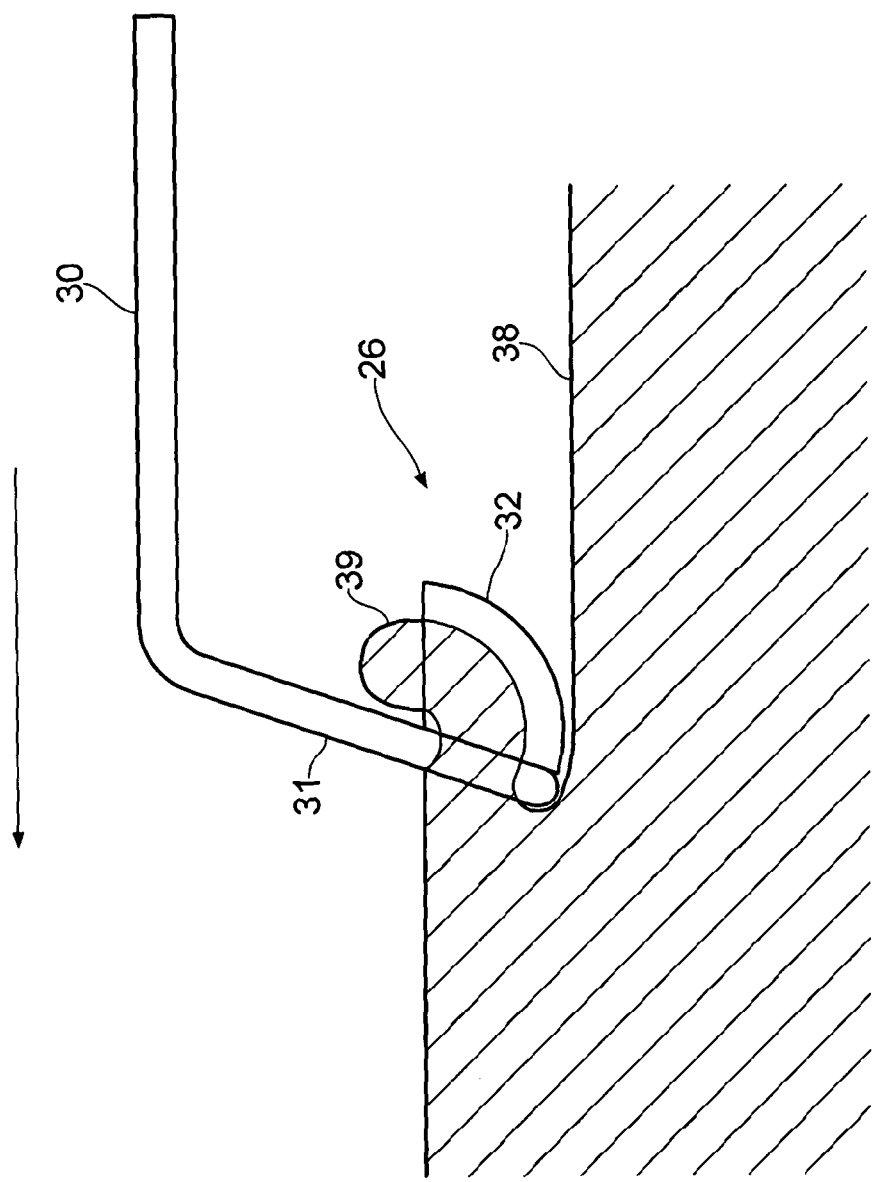
Figure 8:
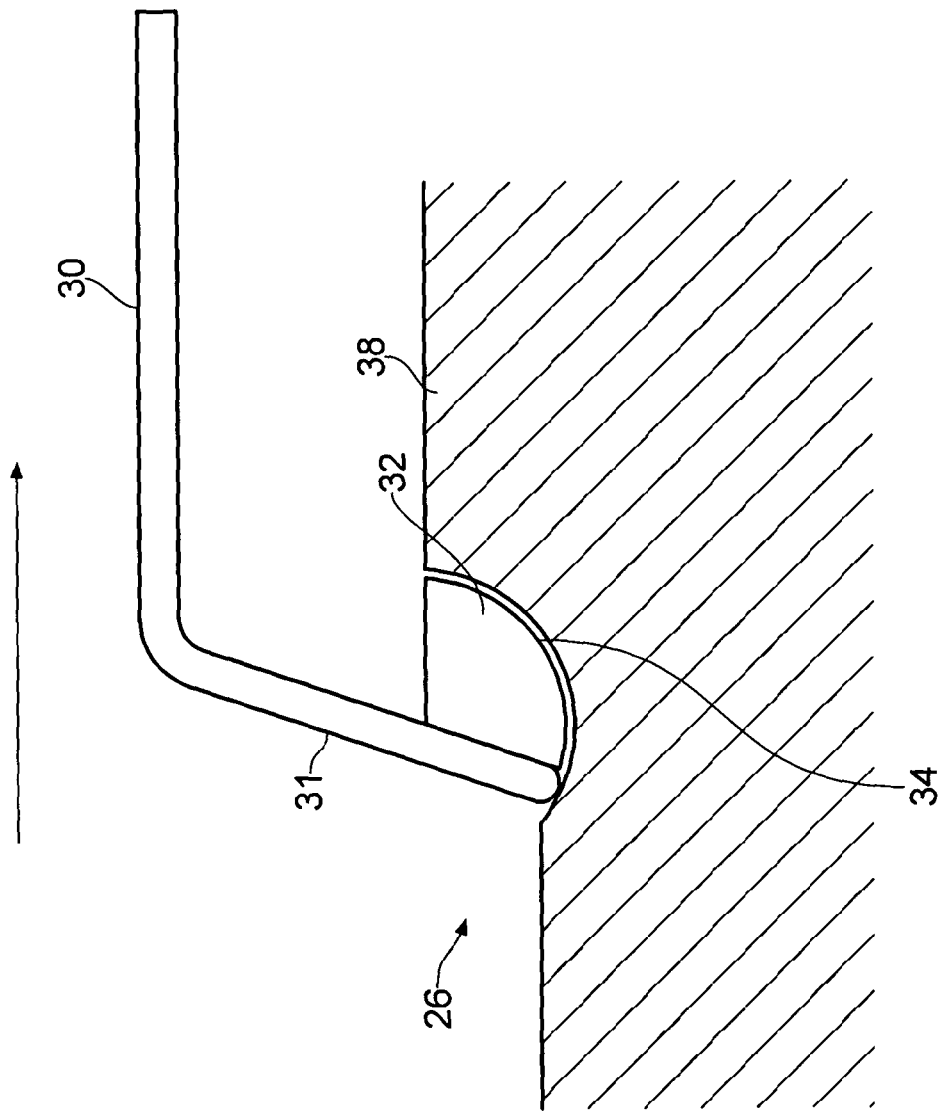
Figure 9:
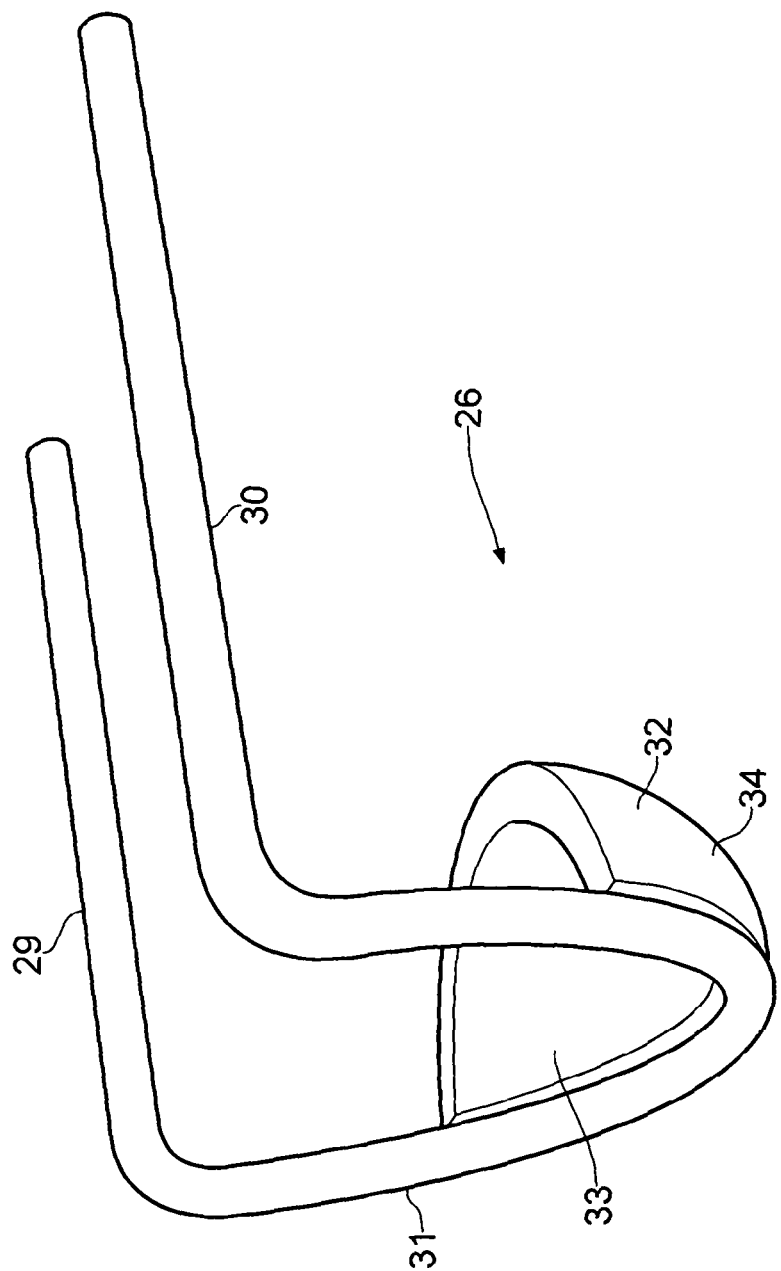
Figure 10:
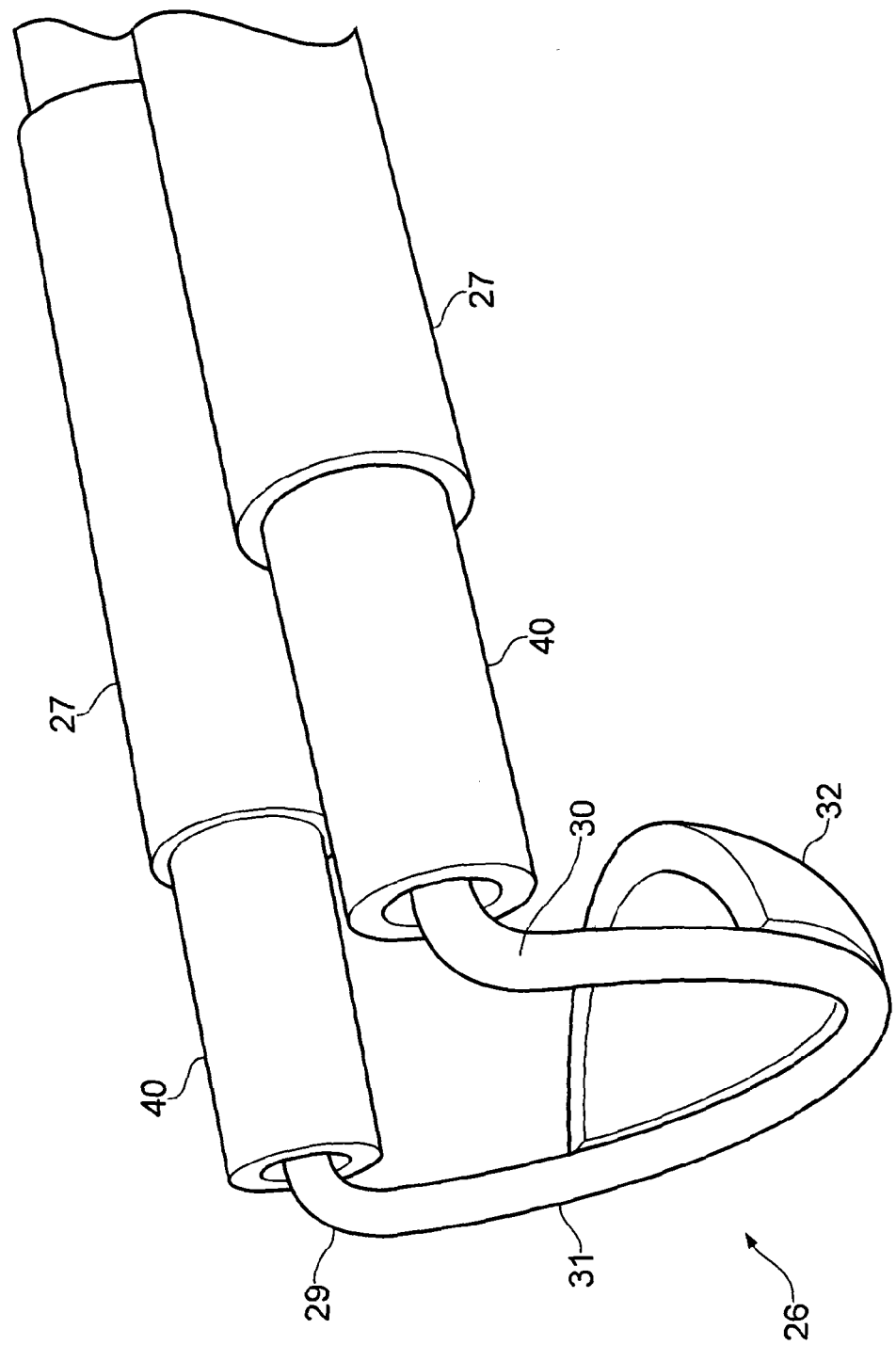
Figure 11:
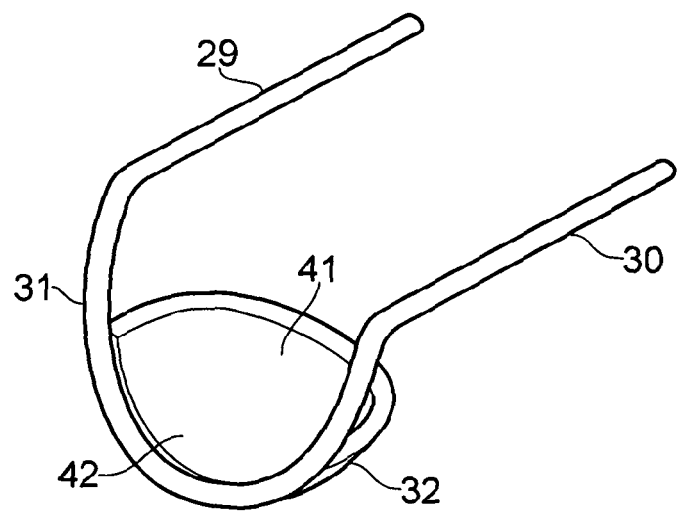
Figure 12:
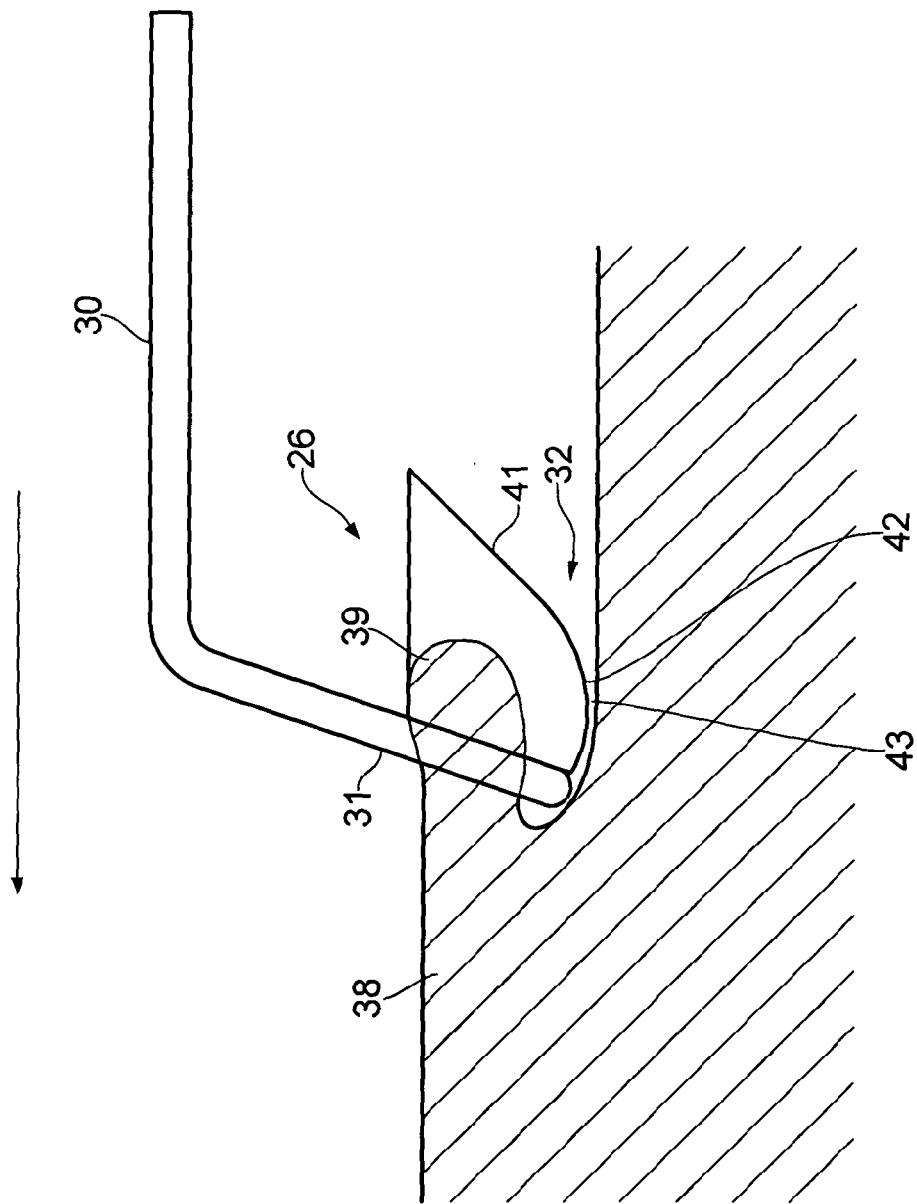
Figure 13:
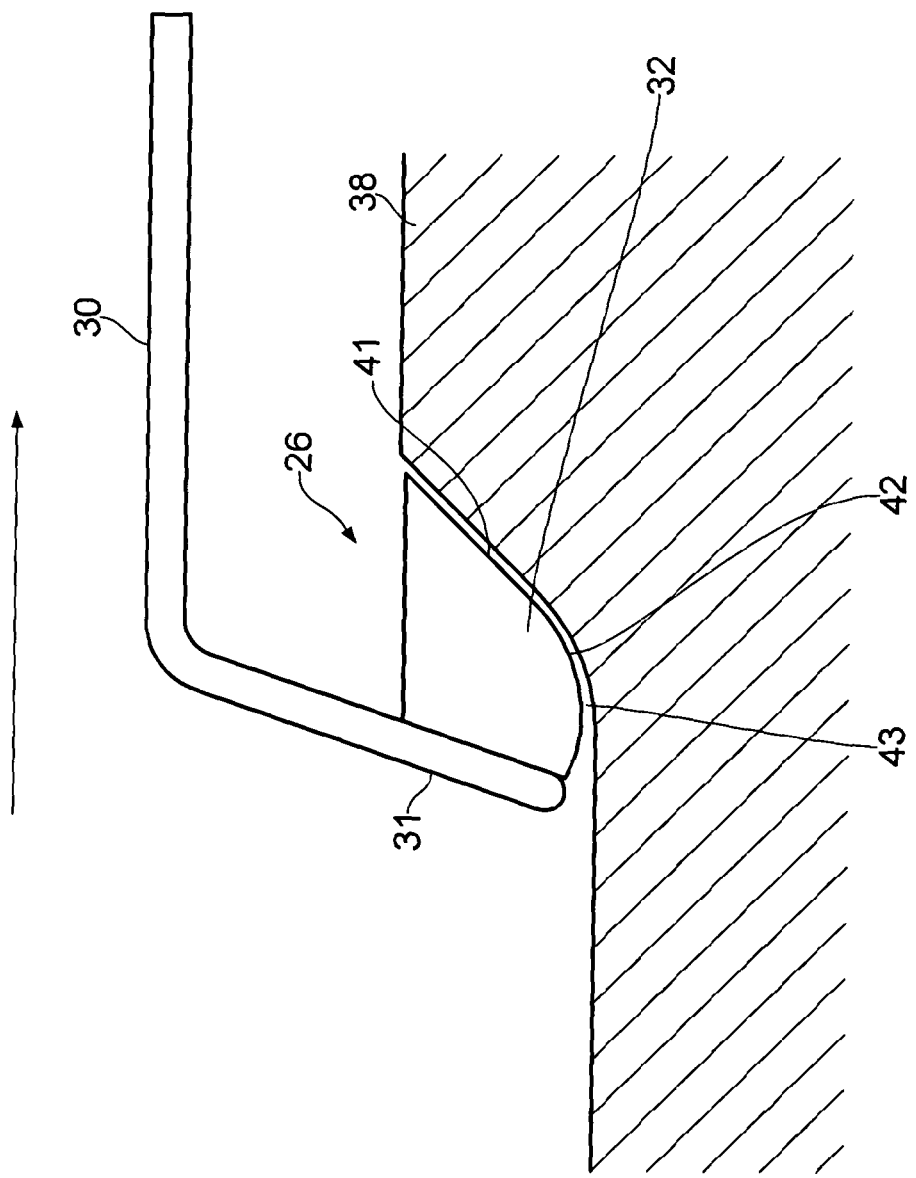
Figure 14:
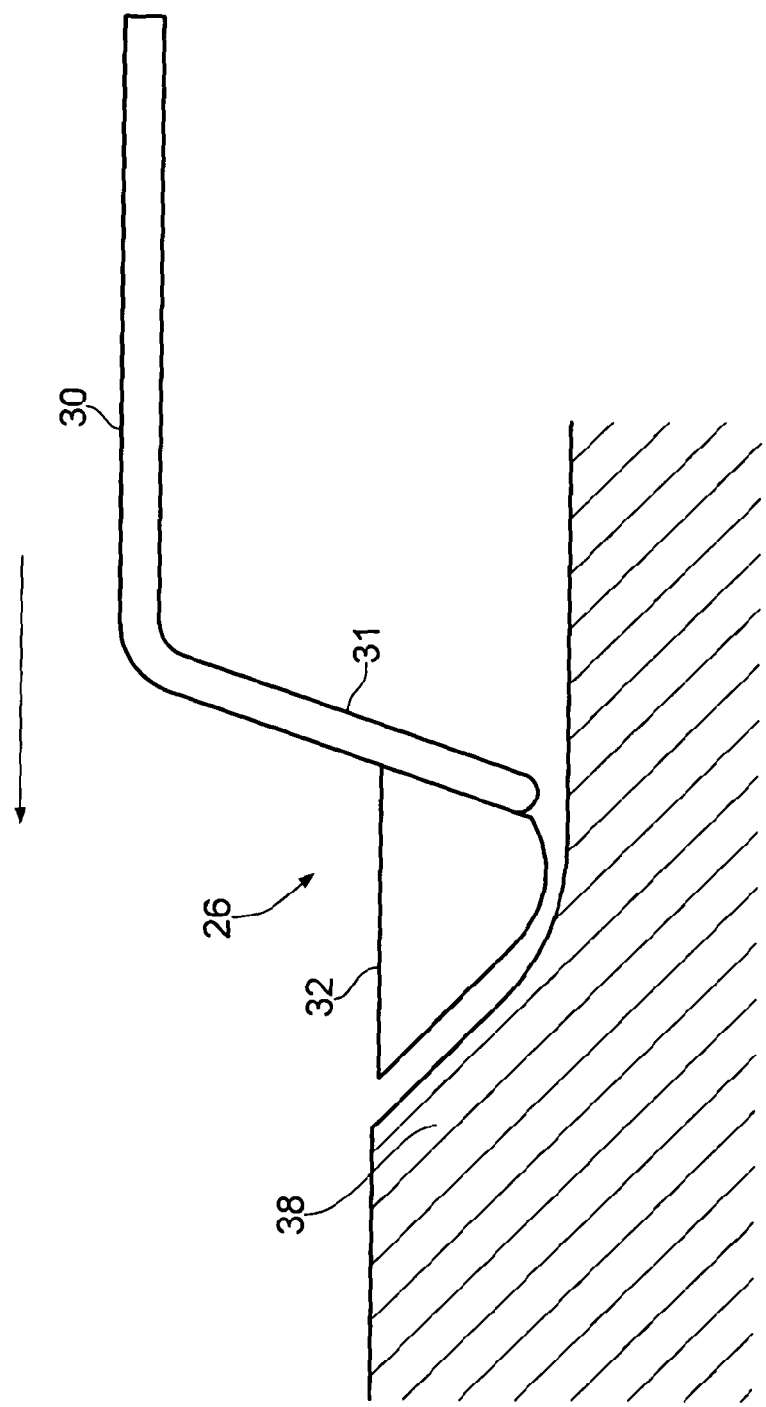
Figure 15:
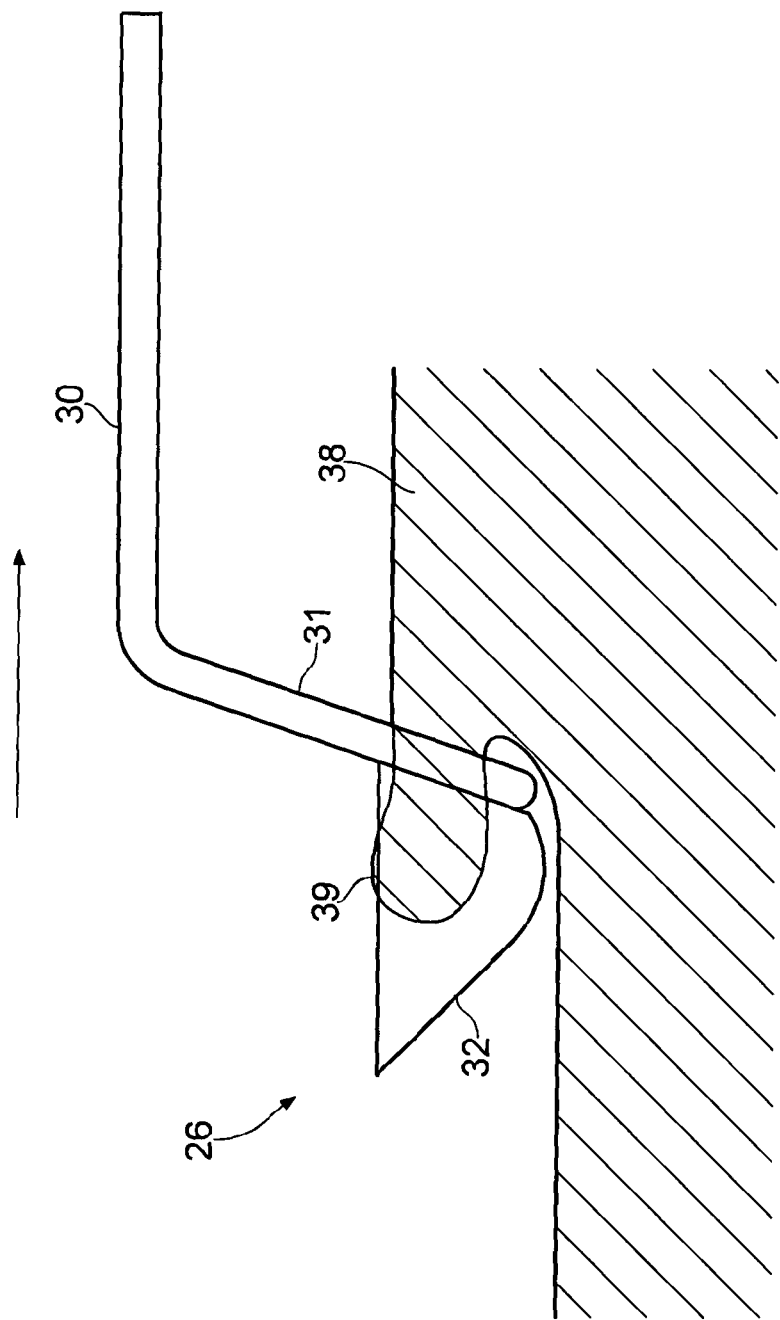

The invention will now be further described, by way of example only, with reference to the accompanying drawings, in which:

FIG. 1 is a perspective view of an electrosurgical system for use with an electrode in accordance with the present invention, FIG. 2 is an exploded view of a resectoscopic instrument used as part of the electrosurgical system of FIG. 1, FIG. 3 is a perspective view of an electrode in accordance with the present invention, FIG. 4 is a schematic sectional view of the electrode of FIG. 3 being used in a first mode of operation, FIG. 5 is a schematic sectional view of the electrode of FIG. 3 being used in a second mode of operation, FIG. 6 is a perspective view of an electrode in accordance with an alternative embodiment of the present invention, FIG. 7 is a schematic sectional view of the electrode of FIG. 6 being used in a first mode of operation, FIG. 8 is a schematic sectional view of the electrode of FIG. 6 being used in a second mode of operation, FIG. 9 is a perspective view of an electrode in accordance with a further embodiment of the present invention, FIG. 10 is a perspective view of the electrode of FIG. 9, shown assembled into a bipolar electrosurgical assembly, FIG. 11 is a perspective view of an electrode in accordance with a further embodiment of the present invention, FIG. 12 is a schematic sectional view of the electrode of FIG. 11 being used in a first mode of operation, FIG. 13 is a schematic sectional view of the electrode of FIG. 11 being used in a second mode of operation, FIG. 14 is a schematic sectional view of a further embodiment of electrode of the present invention being used in a first mode of operation, and FIG. 15 is a schematic sectional view of the electrode of FIG. 14 being used in a second mode of operation.

Referring to FIG. 1, a generator 1 has an output socket 2 providing a radio frequency (RF) output for an instrument 3 via a connection cord 4. Activation of the generator may be performed from the instrument 3 via a connection in cord 4 or by means of a footswitch unit 5, as shown, connected to the rear of the generator by a footswitch connection cord 6. In the illustrated embodiment footswitch unit 5 has two footswitch pedals 7, 8 for selecting a coagulation mode and a cutting/vaporisation mode of the generator respectively. The generator front panel has push buttons 9,10 for respectively setting coagulation and cutting/vaporisation power levels, which are indicated in a display 11. Push buttons 12 are provided as a means for selection between alternative coagulation and cutting/vaporisation waveforms.

As shown in FIG. 2, the instrument 3 is deployed through a resectoscope 13 including an inner sheath 14, an outer sheath 15, and a rod lens telescope/light source assembly 16. The instrument 3 is part of a working element, indicated generally by the reference W and including a bipolar electrode assembly 17.

The sheaths 14, 15 provide for the supply and aspiration of an operating site with a fluid medium via a connector 18. The outer sheath 15 locks over the inner sheath 14, forming a watertight seal. Typically, the inner sheath 14 has a diameter of 24 Fr, and the outer sheath 15 has a diameter of 27 Fr. The telescope assembly 16 provides the means of illuminating and viewing the operative site via a light source (not shown) connected thereto by a connector 19. The viewing angle of the telescope is generally at 30° to its axis.

The working element W may be either passive or active, that is to say the cutting stroke of the electrode may be as the result of a spring bias or against the force of a spring bias. The telescope assembly 16 includes a telescope support tube 20 having a telescope connector 21 at its proximal end, and a sealing block 22 located part way along the support tube 20, the inner sheath 14 being connected to the sealing block. Both of these interfaces are watertight. An electrode support tube 23 is attached to the underside of the telescope support tube 20 on the distal side of the sealing block 22 for the majority of its length. Two spring-loaded links 24 and an insulation block 25, located between the sealing block 22 and the telescope connector 21, make up the mechanism. The active mechanism is arranged so that the spring-loaded links 24 assist the forward stroke, while, in the passive version the links aid the backward stroke. In general, the range of travel is about 25 mm.

The bipolar electrode assembly 17 includes an active electrode 26, to be described in more detail subsequently, and a return electrode 27 located on the shaft of the electrode assembly. The electrodes 26, 27 are connected to the generator 1 via cord 4 connected via socket 28. The electrode support tube 23 is also formed of electrically conductive material, and may constitute a further return electrode, also connected to the generator 1 via cord 4.

Referring to FIG. 3, the active electrode 26 is suspended from two arms 29, 30, and comprises a loop 31 and a vaporisation member 32. The two arms 29, 30 define a longitudinal direction, the loop 31 acting as a downward continuation of the two arms 29, 30, and depending therefrom at an angle of 90 degrees. The vaporisation member 32 is a leaf member in the form of a spherical quadrant, with an upper surface 33 and lower surface 34. Both the upper and lower surfaces are smooth, and the shape of the vaporisation member 32 is that which would be formed by sweeping a lower portion 35 of the loop through an arc of approximately 90 degrees so as to extend both longitudinally on one side of the loop and in a direction towards the arms 29, 30. The vaporisation member 32 is joined to the side of the loop on its proximal side (i.e. lying underneath the arms 29, 30), with the upper surface 33 meeting the loop adjacent its upper periphery 36, and the lower surface 34 meeting the loop adjacent its lower periphery 37. The vaporisation member 32 is thereby integrated with the loop 31, effectively forming a leaf member having one edge which forms a section of the loop spaced from the arms 29, 30. Both the loop 31 and vaporisation member 32 are formed of an electrically conductive material such as tungsten or stainless steel. Other materials, such as platinum, iridium etc., are known in the art as being available for use in high temperature electrodes.

FIGS. 4 and 5 show the electrode 26 of FIG. 3 in the removal of tissue, the tissue being shown generally at 38. FIG. 4 shows the electrode being moved in a forward (distal) direction, such that the first part of the electrode to contact the tissue is the loop 31. An electrosurgical cutting signal supplied to the electrode from the generator 1 causes the loop 31 to cut through the tissue, with a chip of tissue being formed as shown generally at 39. The chip 39 is guided upwardly by the smooth upper surface 33 of the vaporisation member 32, so as to be directed away from the remaining tissue 38.

FIG. 5 shows the electrode of FIG. 3 being moved in a rearward (proximal) direction, such that the first part of the electrode to contact the tissue 38 is the vaporisation member 32. The smooth lower surface 34 of the vaporisation member presents a relatively wide and deep profile to the tissue 38, such that the movement of the electrode 26 causes the formation of a groove or channel of vaporised tissue. The relatively deep profile of the vaporisation member means that the electrode is capable of the bulk vaporisation of tissue, unlike the slider or roller electrodes of the prior art, which tend to be used merely to remove a surface layer of tissue in a "painting" manoeuvre.

The electrode 26 can also be used to perform the surface coagulation of tissue, in which case the electrode is supplied with a coagulation signal from the generator 1, and the electrode is moved over the surface of the tissue 38 with the lower surface 34 of the vaporisation member 32 in contact therewith. Instead of vaporising the tissue, the coagulating signal causes the coagulation of the tissue surface, the relatively smooth and wide nature of the vaporisation member ensuring that coagulation can be performed quickly and effectively. The curved nature of the member 32 means that a groove is produced with a generally rounded profile, as opposed to prior art roller electrodes which tend to form a groove with a rectangular profile. Such rectangular grooves can prove awkward for coagulation purposes, with bleeding occurring in hard to reach corners of the groove. The present device produces a curved groove, and the member 32 can coagulate tissue throughout.

FIG. 6 shows an alternative embodiment of electrode 26, in which the loop 31 depends from the arms 29, 30 at an obtuse angle, approximately 100 degrees as shown in FIG. 6. FIGS. 7 and 8 show the electrode of FIG. 6 being used on tissue in the forward and rearward directions respectively. The operation of the electrode is substantially as described with reference to FIGS. 4 and 5, with a forward movement causing the loop 31 to create chips of tissue, and the rearward movement causing the vaporisation member 32 to create a groove in the tissue 38. An advantage in the obtuse angle of the loop 31 is that it provides an arrangement in which the electrode 26 has its lowest point 43 as part of the curved vaporisation member, making spot coagulation using the electrode easier. The generally upward angle of the loop 31 also helps to ensure that the loop does not become embedded in tissue when moving forward.

FIG. 9 shows a further embodiment of electrode 26, in which the loop 31 depends from the arms 29, 30 at an acute angle, approximately 80 degrees as shown in FIG. 9. FIG. 10 shows the electrode 26 of FIG. 9 together with a return electrode 27, separated from the electrode 26 by means of electrically insulating spacers 40.

FIG. 11 shows a further embodiment in which the vaporisation member 32 has not only a partly spherical profile as in FIGS. 3 to 9, but also a linear section 41. The vaporisation member of FIG. 11 has a curved portion 42 (corresponding to the partly spherical shape of the embodiments of FIGS. 3 to 9), the curved portion 42 lying adjacent the loop 31. However, the curved portion 42 gradually changes into the linear section 41, which continues until the top edge of the vaporisation member 32. This profile is shown more clearly in FIG. 12, which shows the electrode 26 being used in a forward motion to cause the loop 31 to cut a chip 39 in the tissue 38. FIG. 13 shows the electrode being used in a rearward motion to cause the vaporisation member 36 to form a groove in the tissue 38. The linear section 41 creates a straight line area of contact with the tissue 38, allowing more accurate tissue sculpting to take place. The loop 31 depends from the arms 29, 30 at an obtuse angle (approximately 100 degrees), and the vaporisation member 32 is attached to the proximal side of the loop 31.

Finally, FIGS. 14 and 15 show a similar electrode to that of FIGS. 12 and 13, but with the vaporisation member 32 being attached to the distal side of the loop. This means that the electrode 26 vaporises tissue when the electrode is moved in a forward (or distal) direction, and cuts a chip 39 of tissue when moved in a rearward (or proximal) direction. The chips 39 of tissue can be collected by the surgeon to form samples for subsequent biopsy. Each above-described electrode provides a cutting loop for the resection of tissue, and a large area vaporisation electrode for the vaporisation of tissue, the two being provided in a single electrode. Unlike some other arrangements that provide separate electrodes for resection and vaporisation, which must consequently be connected and disconnected in order to provide each function, the present invention provides both functions from a single electrode. However, the surgeon is always confident of which tissue effect is being selected, as the direction of movement of the electrode determines whether a tissue resection or tissue vaporisation effect is achieved.

The electrode 26 is described above as being used with the loop 31 and vaporisation member 32 being disposed below the two arms 29, 30. However, it is equally practical for the electrode to be used in a different orientation, and references herein to "upper" or "lower" should not be construed as implying that only one mode of operation is envisaged. The electrode can in practice be inverted, such that the loop 31 and vaporisation member 32 extend above the two arms, or similarly re-oriented such that the loop 31 and vaporisation member 32 extend sideways therefrom. Whichever method of orientation is used, the movement of the electrode in one longitudinal direction allows the loop to resect tissue, while movement in the opposite longitudinal direction allows the vaporisation member to vaporise and/or coagulate tissue.

The invention claimed is:

1. An electrode in an electrosurgical probe, the electrode comprising
   two arms defining a longitudinal direction,
   a loop extending laterally from the two arms and defining a cutting area within the loop, the loop including a lowest point which is furthest from the two arms, and
   an electrically conductive vaporisation member attached to one side of the loop and electrically connected thereto such that when the loop is supplied with RF energy the vaporisation member is also energised, the vaporisation member including an upper surface and a lower surface and first and second opposing edges, the vaporisation member terminating at the first edge thereof adjacent the loop and then extending upwardly and longitudinally away from the lowest point of the loop so as to terminate at the second edge thereof at a height between the arms and the lowest point of the loop and with the second edge extending from one side of the loop to the other via a point that is longitudinally displaced from the loop, whereby the vaporisation member is such that in use the upper surface thereof does not occlude the cutting area and the lower surface presents a tissue-contacting vaporisation surface when the electrode is moved axially in the longitudinal direction,
   the arrangement being such that when the electrode is energised and moved in a first longitudinal direction, the loop is capable of resecting a sample of tissue, the resected tissue passing through the cutting area and being guided upwardly by the upper surface of the vaporisation member away from the loop, and when the electrode is energised and moved in the opposite longitudinal direction, the vaporisation member is capable of vaporising tissue adjacent to the lower surface thereof to form a groove therein.

2. An electrode according to claim 1, wherein the vaporisation member includes a curved portion of a shape formed by sweeping an arc with a curve equivalent to at least a section of the loop.

3. An electrode according to claim 2, wherein the curved portion of the vaporisation member is of a shape formed by sweeping an arc of at least one of the following:
   45 degrees or more;
   90 degrees or even more; and
   120 degrees.

4. An electrode according to claim 2, wherein the curved portion of the vaporisation member forms part of the surface of a sphere.

5. An electrode according to claim 2, wherein the curved portion constitutes the entirety of the vaporisation member.

6. An electrode according to claim 2, wherein the curved portion constitutes only a portion of the vaporisation member.

7. An electrode according to claim 6, wherein the vaporisation member also includes a linear, upwardly sloping section.

8. An electrode according to claim 7, wherein the curved portion is located between the loop and the upwardly sloping section.

9. An electrode according to claim 1, wherein the cross-sectional thickness of the vaporisation member is substantially constant.

10. An electrode according to claim 1, wherein the loop extends laterally at least one of the following angles from the two arms:
    an angle of between 60 and 120 degrees;
    an angle of less than 90 degrees; and
    an angle of substantially 90 degrees.

11. An electrode according to claim 1, wherein the vaporisation member is attached to the loop on the same side as the two arms.

12. An electrode according to claim 1, wherein the vaporisation member is attached to the loop portion on the opposite side from the two arms.

13. An electrode according to claim 1, forming part of a bipolar electrode assembly that is further provided with a return electrode insulated from the arms and the loop.

14. An electrode according to claim 1, forming part of a monopolar electrosurgery system in which the system is provided with a return patient plate electrode separate from the arms and the loop.

15. A method of treating tissue comprising the steps of
    i) presenting an electrode to tissue to be treated, the electrode comprising
       a) two arms defining a longitudinal direction,
       b) a loop extending laterally from the two arms and defining a cutting area within the loop, the loop including a lowest point which is furthest from the two arms, and
       c) an electrically conductive vaporisation member attached to one side of the loop and electrically connected thereto such that when the loop is supplied with RF energy the vaporisation member is also energised, the vaporisation member including an upper surface and a lower surface and first and second opposing edges, the vaporisation member terminating at the first edge thereof adjacent the loop and then extending upwardly and longitudinally away from the lowest point of the loop so as to terminate at the second edge thereof at a height between the arms and the lowest point of the loop and with the second edge extending from one side of the loop to the other via a point that is longitudinally displaced from the loop, the vaporisation member being such that in use the upper surface thereof does not occlude the cutting area and the lower surface presents a tissue-contacting vaporisation surface when the electrode is moved axially in the longitudinal direction;
    ii) energising the electrode with RF energy,
    iii) moving the electrode in a first longitudinal direction such that the loop resects a sample of tissue, the resected tissue passing through the cutting area and being guided upwardly by the upper surface of the vaporisation member away front the loop, and
    iv) moving the electrode in the opposite longitudinal direction, such that the vaporisation member vaporises tissue adjacent to the lower surface thereof to form a groove therein.

16. A hybrid electrode for an electrosurgical probe, wherein the electrode comprises two support arms defining a longitudinal direction, an electrically conductive cutting loop extending laterally from the arms to define a resection area within the loop, and, integral with the loop, an electrically conductive leaf member having one edge forming at least a section of the loop which is spaced from the arms, the leaf member extending from the said edge both longitudinally on one side of the loop and in a direction towards the arms so as to be angled towards the longitudinal direction with respect to the laterally extending cutting loop, the conductive leaf member having a lower surface that in use provides a conductive vaporisation surface when the electrode is moved in a first longitudinal direction, and an upper surface that in use guides tissue resected by the cutting loop in the resection area away from the cutting loop and towards the arms when the electrode is moved in a second longitudinal direction opposite to the first longitudinal direction.

17. An electrode according to claim 16, wherein the leaf member defines a projected area, in a plane perpendicular to the arms, of a width substantially equal to the width of the loop.

\* \* \* \* \*